US010806359B2

United States Patent
Zeng et al.

(10) Patent No.: US 10,806,359 B2
(45) Date of Patent: Oct. 20, 2020

(54) CONNECTIVITY ANALYSIS FOR ARRHYTHMIA DRIVERS

(71) Applicant: CARDIOINSIGHT TECHNOLOGIES, INC., Independence, OH (US)

(72) Inventors: Qingguo Zeng, Solon, OH (US); Qing Lou, Powell, OH (US); Ryan M. Bokan, Cleveland, OH (US); Ping Jia, Solon, OH (US); Connor S. Edel, Independence, OH (US); Charulatha Ramanathan, Solon, OH (US)

(73) Assignee: CARDIOINSIGHT TECHNOLOGIES, INC., Independence, OH (US)

( * ) Notice: Subject to any disclaimer, the term of this patent is extended or adjusted under 35 U.S.C. 154(b) by 674 days.

(21) Appl. No.: 15/498,992

(22) Filed: Apr. 27, 2017

(65) Prior Publication Data
US 2018/0310850 A1    Nov. 1, 2018

(51) Int. Cl.
*A61B 5/04*    (2006.01)
*A61B 5/044*   (2006.01)

(52) U.S. Cl.
CPC .......... *A61B 5/04012* (2013.01); *A61B 5/044* (2013.01)

(58) Field of Classification Search
CPC ............................. A61B 5/04012; A61B 5/044
USPC ........................................................ 600/515
See application file for complete search history.

(56) References Cited

U.S. PATENT DOCUMENTS

| 7,123,954 B2 | 10/2006 | Narayan et al. |
| 7,729,753 B2 | 6/2010 | Kremliovsky et al. |
| 8,315,698 B2 * | 11/2012 | Cuesta Frau ........ A61B 5/0452 600/515 |
| 8,923,958 B2 | 12/2014 | Gupta et al. |
| 2010/0094274 A1 | 4/2010 | Narayan et al. |

(Continued)

FOREIGN PATENT DOCUMENTS

| WO | 2012037471 | 3/2012 |
| WO | 2012092016 | 7/2012 |

OTHER PUBLICATIONS

Applicant: CardioInsight Technologies, Inc., International Search Report and Written Opinion; Authorized Officer: Yeonkyung Kim; Date of Completion: Aug. 8, 2018; 10 pgs.

(Continued)

*Primary Examiner* — Nadia A Mahmood
(74) *Attorney, Agent, or Firm* — Tarolli, Sundheim, Covell & Tummino LLP (57) ABSTRACT

One or more non-transitory computer-readable media have instructions executable by a processor and programmed to perform a method. The method includes analyzing the electrical data to locate one or more wave front lines over a given time interval. The electrical data represents electrophysiological signals distributed across a cardiac envelope for one or more time intervals. A respective trajectory is determined for each wave end of each wave front line that is located across the cardiac envelope over the given time interval. A set of connected trajectories are identified based on a duration that the trajectories are connected to each other by a respective wave front line during the given time interval. A connectivity association is characterized for the trajectories in the set of connected trajectories.

22 Claims, 7 Drawing Sheets

(56) References Cited

U.S. PATENT DOCUMENTS

| | | |
|---|---|---|
| 2011/0251505 A1 | 10/2011 | Narayan et al. |
| 2013/0006131 A1 | 1/2013 | Narayan et al. |
| 2014/0200822 A1 | 7/2014 | Dubois et al. |
| 2015/0238101 A1 | 8/2015 | Weng et al. |

OTHER PUBLICATIONS

S. V. Pandit et al.: "Rotors and the Dynamics of Cardiac Fibrillation", Circulation Research., vol. 112, No. 5., Feb. 28, 2013, pp. 849-862.

Rogers, et al., Quantitative Techniques for Analyzing High-Resolution Cardiac-Mapping Data; IEEE Engineering in Medicine and Biology. Jan./Feb. 1998 [retrieved Aug. 24, 2014]; Retrieved from the Internet: URL:http://phdtree.org/pdf/1235414-quantitative-techniques-for-analyzing-high-resolution-cardiac-mapping-data/>; pp. 62-72.

Tusscher, et al., "Organization of Ventricular Fibrillation in the Human Heart"; Circulation Research, American Heart Association; May 31, 2007 [retrieved Aug. 27, 2014]; Retrieved from the Internet: URL:http://www-binf.bio.uu.nl/khwituss/Publications/CircRes.pdf; pp. 1-15.

Rogers, et al., Evolution, and Spatial Distribution of Functional Reentry During Ventricular Fibrillation in Pigs. Circulation Research, 84:945-954, American Heart Association. 1999 [retrieved Aug. 28, 2014]. Retrieved from the Internet: URL:http://circres.ahajournals.org/content/84/8/945.full, pp. 945-954.

\* cited by examiner

CONNECTIVITY ANALYSIS FOR ARRHYTHMIA DRIVERS

TECHNICAL FIELD

This disclosure relates to analysis and detection for arrhythmia drivers.

BACKGROUND

Cardiac arrhythmia, also known as dysrhythmia, refers generally to any of a group of conditions in which the electrical activity of the heart is irregular or is faster or slower than normal. Arrhythmias can occur in the upper chambers of the heart, or in the lower chambers of the heart. Arrhythmias may occur at any age. Some are barely perceptible, whereas others can be more dramatic and can even lead to sudden cardiac death. The identification of potential arrhythmogenic sites can help guide treatment.

SUMMARY

This disclosure relates to connectivity analysis for arrhythmia drivers.

As one example, one or more non-transitory computer-readable media have instructions executable by a processor and programmed to perform a method. The method includes analyzing the electrical data to locate one or more wave front lines over a given time interval. The electrical data represents electrophysiological signals distributed across a cardiac envelope for one or more time intervals. A respective trajectory is determined for each wave end of each wave front line that is located across the cardiac envelope over the given time interval. A set of connected trajectories are identified based on a duration that the trajectories are connected to each other by a respective wave front line during the given time interval. A connectivity association is characterized for the trajectories in the set of connected trajectories.

As another example, a system includes memory to store machine readable instructions and data, the data comprising store electrical data representing electrophysiological signals distributed across a cardiac envelope for one or more time intervals. The system also includes a processor to access the memory and execute the instructions. The instructions include a wave front analyzer, a trajectory detector, a connectivity detector and a connectivity characterization function. The wave front analyzer analyzes electrical data for a given time interval to identify a wave front line across the cardiac envelope. The trajectory detector detects a respective trajectory for wave ends of the wave front line over the given time interval. The connectivity detector identifies a set of connected trajectories according to a duration that the trajectories of wave ends are connected to each other by the wave front line over the given time interval. The connectivity characterization function that applies spatial and/or temporal criteria to characterize a connectivity association for trajectories in the set of connected trajectories. An output generator provides output data to drive a display with a graphical representation of the connectivity association for the trajectories in the set of connected trajectories.

In some examples, the systems and methods can store computed information as arrhythmia driver data. The arrhythmia driver data can be employed to generate one or more graphical maps for each such arrhythmia driver. In other examples, the arrhythmia driver data can be used to control a therapy system that is configured to deliver a therapy to a patient.

DETAILED DESCRIPTION

This disclosure relate to detection and analysis of arrhythmia drivers. In one example, one or more wave front lines can be determined across a geometric surface over a time interval and corresponding trajectories can be detected for a given wave front line. The trajectories can trace movement of end points of the given wave front line across the geometric surface over the time interval. The trajectories determined during the time interval can be analyzed to identify one or more sets of connected trajectories. For example, the trajectories can be considered as connected when the trajectories are linked by a common wave front line for at least a predetermined period of time. Systems and methods herein can also apply criteria (e.g., spatial and/or temporal thresholds) to characterize a connectivity association for trajectories in each set of connected trajectories. For instance, the connectivity association for connected trajectories can be classified as a local connectivity association, a far connectivity association or an intermediate association according to the applied connectivity criteria.

To enable user perception based on the detection and analysis, an output generator can generate a graphical map to display information demonstrating the connected trajectories and/or a connectivity association, such as superimposed graphics on a heart model (e.g., a three-dimensional model). In some examples, the analysis and detection may be repeated for electrophysiological signals acquired over a plurality of time intervals to provide a composite indication of connected trajectories. Additionally or alternatively, the process can be repeated during an interactive procedure to help guide treatment to one or more arrhythmogenic sites.

For example, treatment sites can be identified on the graphical map, such as in a region on a cardiac surface residing between a pair of connected trajectories. Various other outputs (e.g., rotation maps) can be generated as well and concurrently or separately displayed. By identifying connected trajectories at sites on the heart, as disclosed herein, treatment at locations where the trajectories are linked occur, such as between connected trajectories, may positively impact arrhythmogenic activity (e.g., atrial fibrillation, atrial tachycardia, ventricular fibrillation, ventricular tachycardia and the like).

While many examples of trajectory detection and analysis are disclosed with respect to reconstructed electrograms on a cardiac envelope, such as a cardiac surface, the systems and methods disclosed herein are equally applicable to any electrical signals for a geometric surface, whether measured directly for the surface by contact or non-contact sensors or derived (e.g., reconstructed) from measurements. Additionally, while many examples herein are described in the context of detection and analysis of cardiac electrical signals, it is to be understood that the approaches disclosed herein are equally applicable to other electrophysiological signals, such as acquired as part of electroencephalography, electromyography, electrooculography and the like. That is, the system and method disclosed herein can be applied to analyze trajectories of correlated parts of the waveform that can be acquired from or calculated for a surface.

Figure 1:
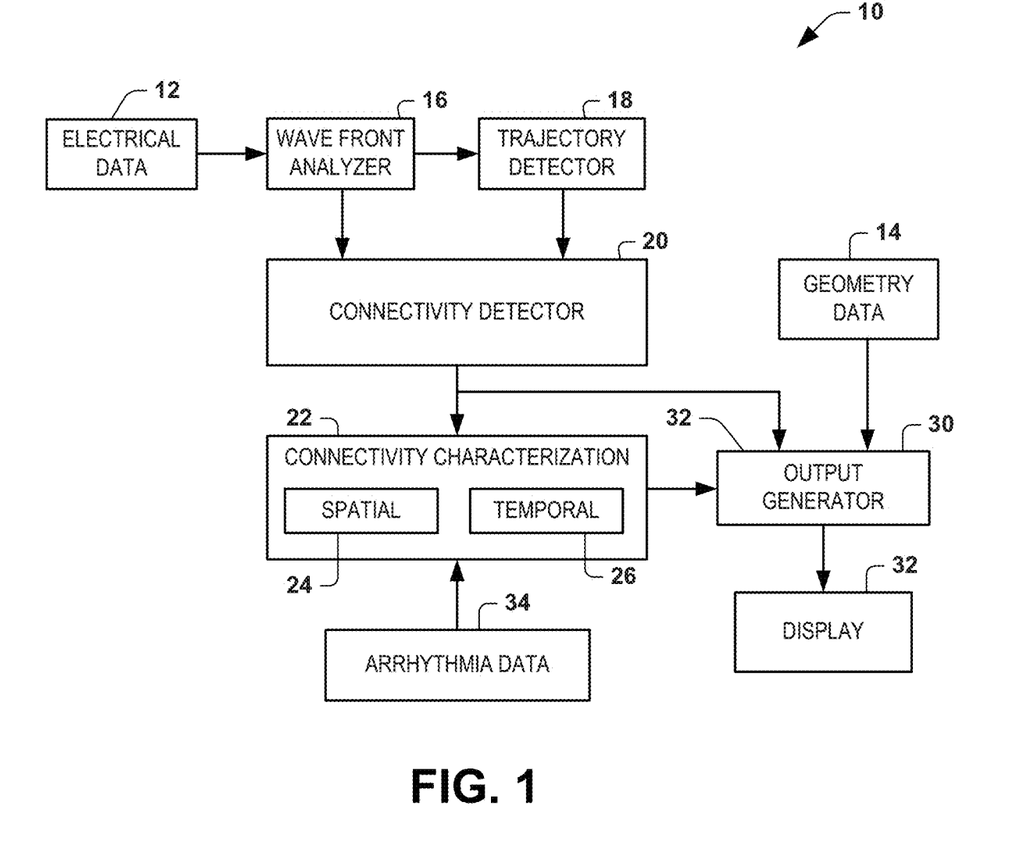
FIG. 1 depicts an example of a system to analyze trajectories for arrhythmia drivers.

FIG. 1 depicts an example of a system 10 to detect and analyze arrhythmia drivers, namely as associations between trajectories. As used herein, in the context of cardiac electrophysiology, the term trajectory can refer to an organized disorganized source of any electrical activity for the heart that remains active and traverses across a cardiac surface for at least some minimum period of time. Thus, the system 10 can analyze electrical data 12, such as electrical signals distributed across the cardiac surface (e.g., the entire heart or one or more regions thereof). The electrical data 12 can be stored in memory (e.g., one or more non-transitory computer readable media). As an example, the electrical data includes geometry information (e.g., corresponding to geometry data 14) for an anatomical surface to provide electroanatomic data that describes electrical activity at a plurality of anatomical locations (e.g., nodes) for one or more time intervals. In some examples, the electrical data 12 can be provided as electrograms or other electrical waveforms representing electrical activity for the nodes distributed across the cardiac surface.

As a further example, the geometry data defines anatomical locations represented as nodes distributed (e.g., an even distribution) over a geometric surface. The geometric surface can be a three-dimensional surface of an anatomical structure, such as tissue of a patient (e.g., human or other animal). In some examples, the patient tissue is cardiac tissue, such that the geometric surface corresponds to an epicardial surface, an endocardial surface or another cardiac envelope, and the electrical data 12 represents signals at nodes on such surface. The geometric surface can be patient specific (e.g., based on imaging data for the patient), it can be a generic model of the surface or it can be a hybrid version of a model that is customized based on patient-specific data (e.g., imaging data, patient measurements, reconstructed data, and/or the like). The electrical data 12 thus can characterize electrical signals for nodes distributed across any such geometric surface. As disclosed herein, the geometric surface containing the nodes at which the electrical signals can be defined by the geometry data 14 that is stored in memory, and may be part of or otherwise associated with the electrical data 12.

As a further example, the electrical data 12 can correspond to electrophysiological signals, such as correspond to physiological signals obtained by one or more electrodes or otherwise derived from such signals. For instance, the electrodes can be applied to measure the electrical activity non-invasively, such as may be positioned over a patient's body surface such as the patient's head (e.g., for electroencephalography), a patient's thorax (e.g., for electrocardiography) or other noninvasive locations. The electrical data thus can correspond to the body surface measured electrical signals or, as disclosed herein, be reconstructed onto another surface based on the body surface measurements. In other examples, the electrical data 12 can be acquired invasively, such as by one or more electrodes positioned within a patient's body (e.g., on a lead or a basket catheter during an EP study or the like). In yet other examples, the input electrical data 12 can include or be derived from a hybrid approach that includes both non-invasively acquired electrical signals and invasively acquired electrical signals.

The electrical data 12 can include electrical activity for nodes on a geometric surface that is defined by the geometry data 14. The geometry data 14 can represent a two-dimensional or a three-dimensional surface for the patient. For example, the geometric surface can be a body surface (e.g., an outer surface of the thorax or portion thereof) where sensors are positioned to measure electrical activity. In other examples, the surface can be a surface of internal tissue or a computed envelope having a prescribed position relative to certain internal tissue. Depending on the geometric surface for which the electrical data 12 is provided, the geometry data 14 can correspond to actual patient anatomical geometry (e.g., derived from one or more imaging technologies, such as x-ray, computed tomography, magnetic resonance imaging or the like), a preprogrammed generic model or a hybrid thereof (e.g., a model that is modified based on patient anatomy). That is, the geometric surface should represent the same surface that contains the nodes where the electrical activity represented by the electrical data 12 resides.

The system 10 also employs a wave front analyzer 16 to identify one or more wave front lines across the geometric surface based on the electrical data 12 for signals over such surface. A wave front line corresponds to a collection of substantially contiguous nodes across the surface having electrical signals that exhibit an activation or depolarization at a respective time. Thus, as the activation or depolarization of nodes propagates across the surface, the nodes can be connected to define a wave front line. At each instant in time (e.g., a time sample index or time frame) while the wave front is active, a segment of nodes along the edge of the wave front defines a wave front line. The wave front line thus extends between a pair of spaced apart end nodes thereof, referred to herein as wave ends (also known as wave break points). In some situations, a wave front may form a closed loop and thus does not have wave ends. As used herein, a wave front line refers to a segment formed of an arrangement of nodes that does not form a loop.

As one example, the wave front analyzer 16 can be implemented to determine wave front locations and wave front lines as disclosed in International application no. PCT/US14/12051, filed on Jan. 17, 2014, and entitled WAVE FRONT DETECTION FOR ELECTROPHYSIOLOGICAL SIGNALS, which is incorporated herein by reference. In other examples, the wave front analyzer 16 may implement different approaches, including non-phase based approaches, to determine the activation times, wave front locations and wave front lines across the surface. One example of a non-phase based approach to determine wave fronts and wave front lines is disclosed in U.S. patent application Ser. No. 15/498,662, filed concurrently with this application on Apr. 27, 2017, and entitled DETECTING CONDUCTION TIMING, which is incorporated herein by reference in its entirety.

A trajectory detector 18 determines trajectories based upon wave front data (representing spatial and timing data for nodes on one or more wave front lines) provided by the wave front analyzer 16. The trajectory detector 18 determines the trajectory for wave ends of each wave front line across the geometric surface (cardiac envelope) during a given time interval. The trajectory for each end in the given time interval can be stored in memory as separate trajectory data.

As an example, the trajectory detector 18 includes machine-readable instructions programmed to identify wave ends of wave front lines in each time sample over one or more time intervals, which may be contiguous or non-contiguous time intervals. For the first time sample, each wave end initializes a new trajectory and each such trajectory will be active. Then for the remaining time samples in the interval, the trajectory detector 18 can identify wave ends from the end nodes of a corresponding wave front line for each subsequent time sample. The trajectory detector 18 can be programmed to evaluate each wave end temporally and spatially to determine whether the wave break point should be added to a respective active trajectory or if such break point should begin another new trajectory. An active trajectory may become inactive, for example, if no wave ends are appended to it for a certain period (e.g., a predetermined or user-programmable duration threshold, such as about 5 ms). After constructing each trajectory in the time interval, the trajectory detector can apply a temporal constraint (e.g., a predetermined or user-programmable duration threshold, such as about 100 ms) so that only trajectories that remain active longer than a prescribed amount of time are stored in memory as trajectory data.

A connectivity detector 20 can determine if a given pair of rotors is connected based on the wave front data (provided by wave front analyzer 16) and the trajectory data (provided by trajectory detector 18) during a given time interval. As used herein, a connection between trajectories refers to an association or link between wave ends resulting from one or more wave front lines that link the pair of identified trajectories temporally and/or spatially across the geometric surface (cardiac envelope). For example, the connectivity detector 20 can ascertain that wave ends are connected in response to determining that the trajectories for such wave ends are linked over a predetermined period of time or some percentage of time that each trajectory is active during one or multiple time intervals. The connectivity detector 20 can track and store (e.g., as metadata describing spatially and/or temporally) an indication of each wave front line to which a corresponding wave end belongs for each respective trajectory that is generated. In response to connectivity detector 20 determining that wave end trajectories specify the same wave front line over a number of time samples (in one or more time intervals), which can be a predetermined minimum threshold number of samples, connectivity between such trajectories can be affirmed and the trajectories can be identified as being connected. If the connectivity detector 20 determines that trajectories do not meet the minimum connectivity criteria (number of samples) during the interval(s), the trajectories are not identified as being connected. The connectivity detector 20 stores the connectivity data in memory to identify each set of connected wave end trajectories during one or more time intervals.

The connectivity characterization function 22 is programmed to characterize a connectivity association for trajectories in each set of connected trajectories (stored as connectivity data). For example, the connectivity characterization function 22 is programmed to quantify a connectivity association between connected trajectories (e.g., indicate how stable the connection/link is temporally during the time interval and/or spatially across the cardiac envelope). The connectivity characterization function 22 can discriminate between a plurality of different types of predetermined connectivity associations for the set of connected trajectories based on a distance between the trajectories. For instance, the connectivity characterization function 22 computes a distance between each of the connected trajectories across the geometric surface (cardiac envelope). The connectivity characterization function 22 applies a spatial threshold to the computed distance ascertain which one of the plurality of different types of predetermined connectivity associations characterizes the connectivity association. In some examples, the connectivity characterization function 22 applies multiple spatial and temporal thresholds to ascertain which one of the plurality of different types of predetermined connectivity associations characterizes the connectivity association. While the connectivity detector 20 and connectivity characterization function 22 are generally described as being separate, such functions can be integrated to apply spatial and temporal criteria to identify and characterize connected trajectories in the manner disclosed herein.

The connectivity characterization function 22 may be programmed to compute the distance between connected trajectories in two or three-dimensional space, such as the distance between nodes where the trajectories reside at a given time index. For example, the distance may be computed as a Euclidean distance (e.g., a straight line) between nodes. As another example, the distance may be computed as a curved distance across the geometric surface mesh, which may be shortest distance along a curved path between end nodes or distance along edges of the mesh along a path between an intervening set of nodes on the geometric surface.

As a further example, since the trajectories for which the distance is being calculated are connected over a plurality of time frames (samples) during a given interval, the connectivity characterization function 22 may compute the distance for each time frame with each pair of wave end points of a wave front line, and the time samples where the distance is less than the specified distance threshold will be counted as connected within the given interval. The time samples where the distance exceeds the specified distance threshold may be considered as not being connected within the given interval. The time indices where the trajectories are connected can be tagged and utilized to further characterize the connectivity (spatially and/or temporally). Additionally or alternatively, the distance between each of the connected trajectories from each time frame may be averaged (e.g., over the total number of samples or duration of connectivity). The averaged center distance between connected trajectories may be used as the distance between trajectories to further characterize the connectivity between trajectories (spatially and/or temporally).

As a further example, the connectivity characterization function 22 discriminates between a plurality of different types of predetermined connectivity associations for trajectories based on applying spatial and/or temporal criteria 24 and 26, respectively, to each set of connected trajectories. The connectivity associations can include a local connectivity association, a far connectivity association and an intermediate connectivity association. Other connectivity associations for connected trajectories may be used in other examples. In this example, the connectivity characterization function 22 specifies the local connectivity association for a set of connected trajectories in response to determining that the distance between the connected trajectories is less than a first spatial threshold (e.g., less than about 3.5 cm). The connectivity characterization function 22 further specifies the far connectivity association for the set of connected trajectories in response to determining that the distance between the connected trajectories exceeds a second threshold (e.g., greater than about 5 cm). Additionally, the connectivity characterization function 22 may specify the intermediate connectivity for the connected trajectories in response to determining that the distance between the connected trajectories is outside of the first and second thresholds. A temporal threshold (e.g., greater than about 70 ms) may also be applied to ensure both temporal and spatial criteria are satisfied for each level of classification. The thresholds may be user programmable.

An output generator 30 can generate one or more outputs to drive (via output interface or port) an associated display 32 with graphical and/or textual information, such as based on wave front data, trajectory data, connectivity data and/or characterization data. For example, the output generator can provide graphical data (that superimposes such connectivity information on a graphical representation of the geometric surface (cardiac envelope) according to the geometry data 14 to render a corresponding electroanatomic map. The map can be a static map that represents information derived from one or more time intervals. As another example, presentation of the graphical maps in a sequence in an order of the time indices can demonstrate dynamic behavior of the trajectories and related connectivity characteristics across the geometric surface. Some example outputs are demonstrated with respect to FIGS. 4-10. While in the example of FIG. 1 the analysis and detection functions 16, 18, 20 and 22 are demonstrated as being separate from the output generator 30, in other examples, the analysis and detection functions could be implemented as a module (e.g., machine readable instructions) that is integrated with output generator.

The output generator 30 further can be configured to rotate the surface geometry (e.g., a 3-D surface) along with any information rendered on the surface in response to a user input. The user-responsive rotation enables a user to selectively reveal other portions of the surface and their wave front activity according to the phase signals that have been computed at such locations, as disclosed herein. Additionally, the graphical map can employ a color coding range or other scale utilized to graphically differentiate between different connectivity associations being mapped onto the geometric surface. As yet a further example, the systems and methods to perform detection of one or more arrhythmia drivers and related rendering in electrocardiographic maps, as disclosed herein, can be combined with other diagnostic and monitoring tools, which may include therapy delivery, to provide an integrated system (see, e.g., FIG. 3).

The connectivity characterization function 22 further may be programmed to prioritize one of the predetermined connectivity associations for trajectories over others, such as based on arrhythmia data 34. The arrhythmia data 34 may be set or be selected in response to a user input, for example, specifying an underlying type of arrhythmia belonging to a patient from which the electrical data 12 is acquired and being analyzed via the system 10. For instance, other means, which may be implemented by the system 10 or separately, can be employed to diagnose the underlying arrhythmia. If more than one type of arrhythmia may be present, connectivity characteristics associated with each may be analyzed separately or in combination by overlaying multiple prioritized output data sets concurrently on the display (e.g., differentiated graphically).

As an example, if the arrhythmia data 34 specifies a micro re-entrant circuit as the cause of the arrhythmia (e.g., atrial fibrillation), then the connectivity characterization function may prioritize local connectivity associations. For instance, the connectivity characterization function 22 can tag local connectivity associations in response to the arrhythmia data and the output generator can identify the region between such locations as a target site in the graphical map. As another example, if the arrhythmia data 34 specifies macro reentry as the major cause of an arrhythmia (e.g., atrial tachycardia), then far connectivity connections are of interest, which the connectivity characterization function 22 can tag in the connectivity data to enable prioritized display of such connectivity information. Local arrhythmogenic tissue that is identified (by connectivity characterization function 22) in the arrhythmia data 34 may further be associated with and used to prioritize local connectivity associations or unstable connectivity associations, for example.

As another example, when a particular type of connectivity association is prioritized over one or more other types, each of the types of associations that is not being prioritized may be set to a non-display condition such that corresponding connectivity associations (that have been determined) are not rendered in the output that is generated by output generator 30. In this way, a user is only shown information about the connectivity association that is being prioritized (e.g., based on the arrhythmia data 34). In other examples, all the connectivity association data may be displayed and the prioritized information can be graphically emphasized (e.g., by color coding or bold lines) over the non-prioritized information that has been determined for the relevant time interval(s).

Figure 2:
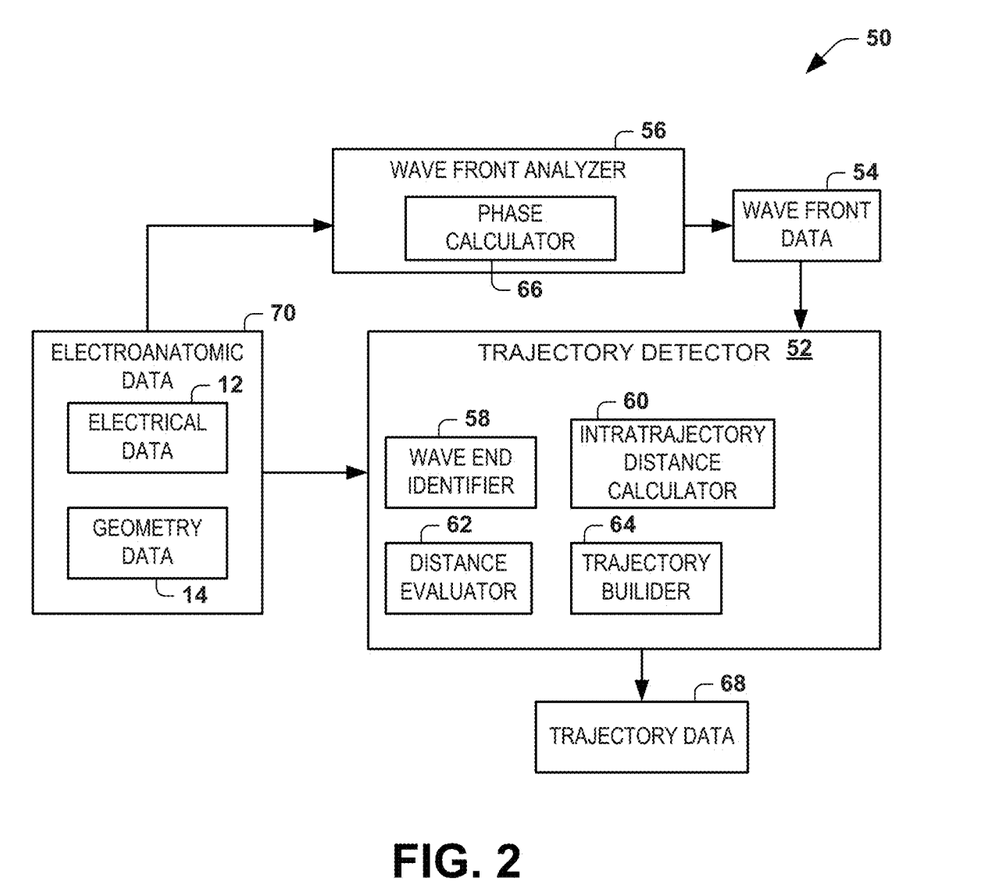
FIG. 2 depicts an example of a system to detect trajectories.

FIG. 2 depicts an example of a system 50 that may be implemented to detect one or more trajectories across a surface geometry (cardiac envelope). The detection system 50 includes a trajectory detector 52 that can be implemented as the trajectory detector 18 in the system 10 of FIG. 1. In the example of FIG. 2, the trajectory detector 52 can be programmed to detect trajectories based on wave front data 54. The wave front data 54 is computed by a wave front analyzer 56, which can be implemented by wave front analyzer 16 of FIG. 1. In the example of FIG. 2, the trajectory detector 52 can include executable code blocks demonstrated as a wave end identifier 58, a distance calculator 60, a distance evaluator 62 and a trajectory builder 64. The trajectory detector 52 executes code blocks 58, 60, 62 and 64 to generate trajectory data 68 for wave ends across the geometric surface during one or more time intervals.

In the example of FIG. 2, the wave front analyzer 56 can employ a phase calculator 66 to compute phase of electrical activity for nodes distributed across the geometric surface (cardiac envelope), such as corresponding to patient tissue, based on the data 68 representing the electrical activity for the geometric surface over time (e.g., one or more time intervals of a plurality of sequential samples of electrical activity). In some examples, the geometric surface can be represented as a mesh including a plurality of nodes interconnected by edges to define the mesh.

By way of further example, the phase calculator 66 can be programmed to convert each cycle of electrical signal into a periodic signal as a function of time. For example, the phase calculator 66 can assign each point in time in between the beginning and end of each cycle a phase value, such as between [−π and π] in an increasing manner. The phase calculator 66 can compute the phase information for several time intervals at various points in time to make the analysis robust in terms of temporal and spatial consistency. In some examples, such as for where the electrical data corresponds to or is derived from non-invasively acquired electrical signals, the phase calculator 66 can provide corresponding phase data for each location (e.g., about 2000 or more nodes) distributed across the cardiac envelope for one or more time intervals for which the electrical data has been acquired. Since the electrical signals can be measured and/or derived concurrently for an entire geometric region (e.g., up to the entire heart surface), the computed phase data and resulting wave front likewise are spatially and temporally consistent across the geometric region of interest.

One example of how the calculator can determine phase based on electrical data 12 for a surface is disclosed in PCT Application No. PCT/US13/60851 filed Sep. 20, 2013, and entitled PHYSIOLOGICAL MAPPING FOR ARRHYTHMIA, which is incorporated herein by reference. Other approaches could also be utilized to determine phase, however. The computed phase information provided by the phase calculator 66 can be stored in memory (e.g., as phase data) and utilized by the wave front analyzer 56 to generate the wave front data 54. As one example, the wave front analyzer may be implemented according to the above-incorporated PCT/US14/12051, among other approaches.

For example, the wave front analyzer 56 can be programmed with machine-readable instructions to compute and identify wave front locations and, in turn, corresponding wave front lines based the phase computed (by phase calculator 66) for the signals across the geometric surface (e.g., at nodes on a cardiac envelope) during one or more time intervals. For instance, the wave front analyzer 56 determines that an activation time or depolarization for each node begins at a time where the phase signal for a given node on the geometric surface crosses a selected phase value $\Phi_S$, which can define a phase threshold. The phase threshold $\Phi_S$ for determining an activation or depolarization boundary condition can be fixed for a given application or it can be programmable, such as in response to a user input. The wave front analyzer 56 further can determine which pairs of neighboring (adjacent) nodes across the surface have phase values encompassing the selected phase value $\Phi_S$ the selected phase value at a given time index. In this context, the term encompass means that the selected phase value $\Phi_S$ lies at or between the phase values for such pair of nodes. The term adjacent nodes can refer to nodes that are interconnected to each other by an edge of a meshed surface, for example, or be located within a predetermined distance of each other (e.g., computed by an instance of distance calculator 60). For the example where the geometric surface is represented as a mesh of nodes interconnected by edges, the wave front analyzer 56 can determine if the selected phase value $\Phi_S$ is between the phase values T and T for a pair of adjacent nodes i and j connected by a common edge of the mesh (e.g., $\Phi_i \leq \Phi_S \leq \Phi_j$ or $\Phi_i \geq \Phi_S \geq \Phi_j$). This determination can be repeated for each interconnected node pair across the geometric surface of interest to identify node pairs that encompass the wave front for one or more time intervals.

The wave front analyzer 56 further can determine a location for the wave front across the geometric surface for each time sample index. For example, the wave front location at a given time resides on a path extending between each of the end node pairs identified as encompassing the selected phase value $\Phi_S$. For each time index (e.g., sample time), the wave front analyzer 56 can identify a plurality of points that estimate an activation or depolarization time across a geometric surface. These points collectively can define a wave front across the surface for each of a plurality of time indices, and the wave front analyzer 56 can connect such points to provide a corresponding wave front line for a given time index. For example, the wave front analyzer 56 further can be programmed to connect each of the plurality of estimated wave front nodes by marching through each of the edges of the mesh determined to contain the selected phase value $\Phi_S$. The points through each edge can thus correspond to an intersection point of each edge, and the intersection points (nodes on the mesh) can be connected together to represent a corresponding wave front at a given time index. The wave front analyzer 56 can provide wave front data 54 that specifies the nodes corresponding to wave front locations and corresponding wave front lines at each time index during the time intervals specified by the electrical data 12, including end nodes for each wave front line.

As a further example, the wave end identifier 58 of the trajectory detector 52 is programmed to identify end points from wave front lines determined (by wave front analyzer 56) on the geometric surface for each time sample. For instance, the wave end identifier 58 can identify end points for each wave front line generated for a given time frame that does not form a loop (e.g., it defines a segment with spaced apart ends). For the first time sample in a given interval (including multiple time samples), the trajectory detector 52 can set each wave end point to initialize a new trajectory and each such trajectory will be active (at least initially). Then for the remaining time samples in the interval, the wave end identifier 58 can determined wave ends in a similar manner, namely from the end points of corresponding wave front lines for each subsequent time sample.

The distance calculator 60 can be programmed to compute an intratrajectory distance (at least spatially) to determine whether the wave end should be added to a respective trajectory or be omitted. For example, the distance calculator 60 can compute the distance for each wave end in a current time sample with respect to a prior location of all active trajectories from one or more previous time samples. The distance can be entirely spatial, such as a Euclidean distance computed in two or three-dimensional coordinate space of the surface geometry, and/or geodesic distance defined along the surface. In other examples, the distance can also account for the temporal distance (e.g., by tracking the time difference or absolute time for each end point). The distance evaluator 62 can be programmed to identify the closest active trajectory (from a previous time sample in the given interval) based on the distance values computed by the distance calculator 60. The distance evaluator 62 evaluates the computed distance (from calculator 60) between the current end points and respective wave front line in one or more prior samples, such as by comparing the computed distance to one or more distance thresholds.

The trajectory builder 64 can be programmed to construct trajectories from wave end points identified in the current time sample by appending (or not appending) each such wave end points to an active trajectory. For instance, the trajectory builder 64 can determine whether the closest active trajectory (determined by the distance evaluator 62)

has yet been updated for the current time sample. If the closest active trajectory to a given wave end has not yet been updated, the trajectory builder 64 can determine if the distance to such closest active trajectory is less than a predetermined threshold (e.g., about 1 cm to about 2 cm). If it is closer than such threshold, the trajectory builder 64 can append the wave end to the closest trajectory that has been identified (e.g., that is within the distance threshold and has not yet been updated). If the trajectory builder determines that the closest, not yet updated wave end is not within the threshold, the trajectory detector 52 can begin a new trajectory using this wave end as the initial wave end of such new trajectory. If the closest active trajectory has already been updated, the trajectory builder 64 can branch out to begin a new trajectory from the given wave end.

The trajectory detector 52 thus can repeat the foregoing process by executing the distance calculator 60, distance evaluator 62 and trajectory builder 64 through the all of the wave ends in the current time interval. Additionally, the trajectory detector 52 can control the state (e.g., active or inactive) of each trajectory during the process. For example, if after going through such wave ends any trajectory that was active in a previous time frame is not updated by this process for the current time frame (or is not updated across a prescribed number of consecutive time samples), the trajectory detector 52 can change the state of such trajectory from an active to an inactive state. The trajectory detector 52 thus stores as the trajectory data 68 in memory to include, for example, state, location and timing information for wave ends that form each trajectory as determined based on one or more time intervals of the wave front data 54. The connectivity detector 20 and connectivity characterization function 22 (FIG. 1) further analyze the wave front data 54 and the trajectory data 68 to detect and characterize connected trajectories as disclosed herein.

Figure 3:
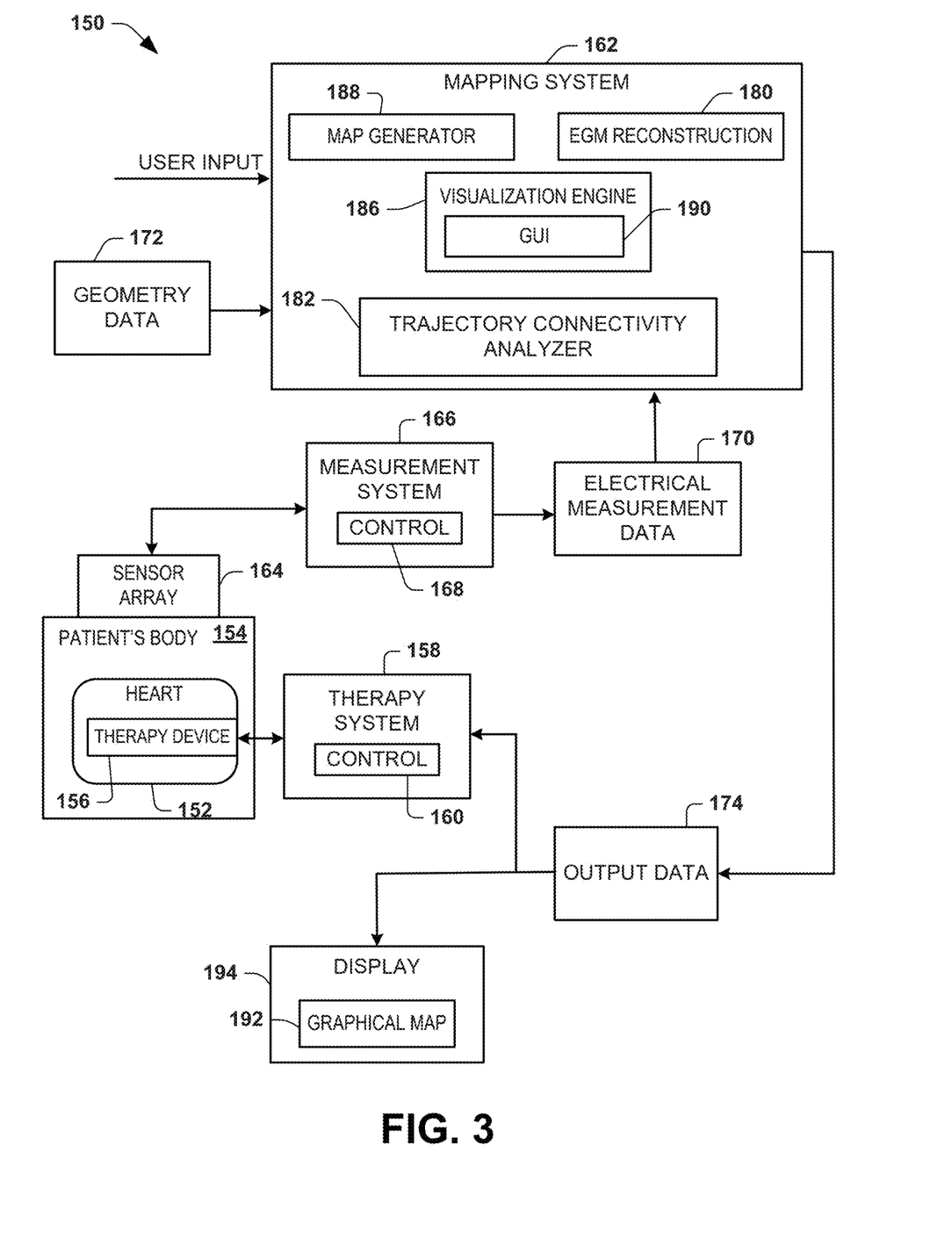
FIG. 3 depicts an example of a mapping and treatment system.

FIG. 3 depicts an example of a system 150 that can be utilized for performing medical testing (diagnostics, screening and/or monitoring) and/or treatment of a patient. In some examples, the system 150 can be implemented to generate corresponding maps for a patient's heart 152 in real time as part of a diagnostic procedure (e.g., an electrophysiology study) to help assess the electrical activity and identify arrhythmia drivers for the patient's heart corresponding to connected trajectories. Additionally or alternatively, the system 150 can be utilized as part of a treatment procedure, such as to help a physician determine parameters for delivering a therapy to the patient (e.g., delivery location, amount and type of therapy) based on one or more identified connected trajectories.

As an example, a catheter having one or more therapy delivery devices 156 affixed thereto can be inserted into a patient's body 154 as to contact the patient's heart 152, endocardially or epicardially. The placement of the therapy delivery device 156 can be guided according to the location and characteristics of connected trajectories that have been identified, such as disclosed herein. The guidance can be automated, semi-automated or be manually implemented based on information provided. Those skilled in the art will understand and appreciate various type and configurations of therapy delivery devices 156 that can be utilized, which can vary depending on the type of treatment and the procedure. For instance, the therapy device 156 can be configured to deliver electrical therapy, chemical therapy, sound wave therapy, thermal therapy or any combination thereof.

By way of example, the therapy delivery device 156 can include one or more electrodes located at a tip of an ablation catheter configured to generate heat for ablating tissue in response to electrical signals (e.g., radiofrequency energy) supplied by a therapy system 158. In other examples, the therapy delivery device 156 can be configured to deliver cooling to perform ablation (e.g., cryogenic ablation), to deliver chemicals (e.g., drugs), ultrasound ablation, high-frequency ablation, or a combination of these or other therapy mechanisms. In still other examples, the therapy delivery device 156 can include one or more electrodes located at a tip of a pacing catheter to deliver electrical stimulation, such as for pacing the heart, in response to electrical signals (e.g., pacing pulses) supplied by the therapy system 158. Other types of therapy can also be delivered via the therapy system 158 and the invasive therapy delivery device 156 that is positioned within the body.

As a further example, the therapy system 158 can be located external to the patient's body 154 and be configured to control therapy that is being delivered by the device 156. For instance, the therapy system 158 includes controls (e.g., hardware and/or software) 160 that can communicate (e.g., supply) electrical signals via a conductive link electrically connected between the delivery device (e.g., one or more electrodes) 156 and the therapy system 158. The control system 160 can control parameters of the signals supplied to the device 156 (e.g., current, voltage, repetition rate, trigger delay, sensing trigger amplitude) for delivering therapy (e.g., ablation or stimulation) via the electrode(s) 154 to one or more location of the heart 152. The control circuitry 160 can set the therapy parameters and apply stimulation based on automatic, manual (e.g., user input) or a combination of automatic and manual (e.g., semiautomatic) controls, which may be based on the detection and associated characteristics of connected trajectories on the cardiac envelope. One or more sensors (not shown) can also communicate sensor information from the therapy device 156 back to the therapy system 158. The position of the device 156 relative to the heart 152 can be determined and tracked intraoperatively via an imaging modality (e.g., fluoroscopy, x-ray), a mapping system 162, direct vision or the like. The location of the device 156 and the therapy parameters thus can be combined to determine and control corresponding therapy parameter data.

Before, during and/or after delivering a therapy via the therapy system 158, another system or subsystem can be utilized to acquire electrophysiology information for the patient. In the example of FIG. 3, a sensor array 164 includes one or more electrodes that can be utilized for recording patient electrical activity. As one example, the sensor array 164 can correspond to a high-density arrangement of body surface sensors (e.g., greater than approximately 200 electrodes) that are distributed over a portion of the patient's torso for measuring electrical activity associated with the patient's heart (e.g., as part of an electrocardiographic mapping procedure). An example of a non-invasive sensor array that can be used is shown and described in International application No. PCT/US2009/063803, filed 10 Nov. 2009, which are incorporated herein by reference. Other arrangements and numbers of sensing electrodes can be used as the sensor array 164. As an example, the array can be a reduced set of electrodes, which does not cover the patient's entire torso and is designed for measuring electrical activity for a particular purpose (e.g., an array of electrodes specially designed for analyzing atrial fibrillation and/or ventricular fibrillation) and/or for monitoring electrical activity for a predetermined spatial region of the heart (e.g., atrial region (s) or ventricular region(s)).

One or more sensors may also be located on the device 156 that is inserted into the patient's body. Such sensors can be utilized separately or in conjunction with the non-invasive sensors 164 for mapping electrical activity for an endocardial surface, such as the wall of a heart chamber, as well as for an epicardial surface. Additionally, such electrode can also be utilized to help localize the device 156 within the heart 152, which can be registered into an image or map that is generated by the system 150. Alternatively, such localization can be implemented in the absence of emitting a signal from an electrode within or on the heart 152.

In each of such example approaches for acquiring patient electrical information, including invasively, non-invasively, or a combination of invasive and non-invasive sensing, the sensor array(s) 164 provide the sensed electrical information to a corresponding measurement system 166. The measurement system 166 can include appropriate controls and associated circuitry 168 for providing corresponding measurement data 170 that describes electrical activity detected by the sensors in the sensor array 164. The measurement data 170 can include analog and/or digital information (e.g., corresponding to electrical data 12).

The control 168 can also be configured to control the data acquisition process (e.g., sample rate, line filtering) for measuring electrical activity and providing the measurement data 170. In some examples, the control 168 can control acquisition of measurement data 170 separately from the therapy system operation, such as in response to a user input. In other examples, the measurement data 170 can be acquired concurrently with and in synchronization with delivering therapy by the therapy system, such as to detect electrical activity of the heart 152 that occurs in response to applying a given therapy (e.g., according to therapy parameters). For instance, appropriate time stamps can be utilized for indexing the temporal relationship between the respective measurement data 170 and therapy parameters use to deliver therapy as to facilitate the evaluation and analysis thereof.

The mapping system 162 is programmed to combine the measurement data 170 corresponding to electrical activity of the heart 152 with geometry data 172 (e.g., corresponding to geometry data 14) by applying appropriate processing and computations to provide corresponding output data 174. As an example, the output data 174 can represent one or more connected trajectories (e.g., trajectory pairs) determined from the electrical measurement data 170 acquired for the patient over one or more time intervals. As disclosed herein, connected trajectories detected and characterized over one or more time intervals can localize identify arrhythmia drivers across the heart 152. The output data 174 can include one or more graphical maps demonstrating determined arrhythmia drivers with respect to a geometric surface of the patient's heart 152 (e.g., trajectory information superimposed on a surface of the heart 152).

Since the measurement system 166 can measure electrical activity of a predetermined region or the entire heart concurrently (e.g., where the sensor array 164 covers the entire thorax of the patient's body 154), the resulting output data (e.g., visualizing attributes of identified stable rotors and/or other electrocardiographic maps) thus can also represent concurrent data for the predetermined region or the entire heart in a temporally and spatially consistent manner. The time interval for which the output data/maps are computed can be selected based on user input (e.g., selecting a timer interval from one or more waveforms). Additionally or alternatively, the selected intervals can be synchronized with the application of therapy by the therapy system 158.

For the example where the electrical measurement data is obtained non-invasively (e.g., via body surface sensor array 164), electrogram reconstruction 180 can be programmed to compute an inverse solution and provide corresponding reconstructed electrograms based on the process signals and the geometry data 172. The reconstructed electrograms thus can correspond to electrocardiographic activity across a cardiac envelope, and can include static (three-dimensional at a given instant in time) and/or be dynamic (e.g., four-dimensional map that varies over time). Examples of inverse algorithms that can be utilized in the system 10 include those disclosed in U.S. Pat. Nos. 7,983,743 and 6,772,004, which are incorporated herein by reference. The EGM reconstruction 180 thus can reconstruct the body surface electrical activity measured via the sensor array 164 onto a multitude of locations on a cardiac envelope (e.g., greater than 1000 locations, such as about 2000 locations or more), such as corresponding to electrical data 12 and associated geometry data 14. In other examples, the mapping system 162 can compute electrical activity over a sub-region of the heart based on electrical activity measured invasively, such as via a basket catheter or other form of measurement probe, to provide corresponding electrical data.

As disclosed herein, the cardiac envelope can correspond to a three dimensional surface geometry corresponding to a patient's heart, which surface can be epicardial or endocardial. Alternatively or additionally, the cardiac envelope can correspond to a geometric surface that resides between the epicardial surface of a patient's heart and the surface of the patient's body where the sensor array 164 has been positioned. Additionally, the geometry data 172 that is utilized by the electrogram reconstruction 180 can correspond to actual patient anatomical geometry, a preprogrammed generic model or a combination thereof (e.g., a model that is modified based on patient anatomy).

As an example, the geometry data 172 may be in the form of graphical representation of the patient's torso, such as image data acquired for the patient. Such image processing can include extraction and segmentation of anatomical features, including one or more organs and other structures, from a digital image set. Additionally, a location for each of the electrodes in the sensor array 164 can be included in the patient geometry data 172, such as by acquiring the image while the electrodes are disposed on the patient and identifying the electrode locations in a coordinate system through appropriate extraction and segmentation. Other non-imaging based techniques can also be utilized to obtain the position of the electrodes in the sensor array, such as a digitizer or manual measurements.

As mentioned above, the geometry data 172 can correspond to a mathematical model, such as can be a generic model or a model that has been constructed based on image data for the patient. Appropriate anatomical or other landmarks, including locations for the electrodes in the sensor array 164 can be identified in the geometry data 172 to facilitate registration of the electrical measurement data 170 and performing the inverse method thereon. The identification of such landmarks can be done manually (e.g., by a person via image editing software) or automatically (e.g., via image processing techniques). By way of further example, the geometry data 172 can be acquired using nearly any imaging modality based on which a corresponding representation of the geometrical surface can be constructed, such as described herein. Such imaging may be performed concurrently with recording the electrical activity that is utilized to generate the patient measurement data 170 or the imaging can be performed separately (e.g., before or after the measurement data has been acquired).

Following (or concurrently with) determining electrical potential data (e.g., electrogram data computed from non-invasively and/or invasively acquired measurements) across the geometric surface of the heart 152, the electrogram data can further undergo signal processing by mapping system 162 to generate the output data, which may include one or more graphical maps. The mapping system 162 can include a trajectory connectivity analyzer method 182 (e.g., corresponding to connectivity detector 20, 52 and/or connectivity characterization function 22) for identifying and/or characterizing connected trajectories, such as disclosed herein. The trajectory connectivity analyzer 182 can also be programmed to compute other information associated with connected trajectories, such as temporal and/or spatial characteristics.

A map generator 188 can be programmed to generate graphic maps for display based on the computed output data 174. A visualization engine 184 can control the display. For instance, parameters associated with the displayed graphical representation, corresponding to an output visualization of the computed map, such as including selecting a time interval, temporal and spatial thresholds, the type of information that is to be presented in the display 194 and the like can be selected in response to a user input via a graphical user interface (GUI) 190. For example, a user can employ the GUI 190 to selectively program one or more parameters (e.g., temporal and spatial thresholds, filter parameters and the like) utilized by the trajectory connectivity analyzer 182 and/or to select one or more sample time intervals to set a time duration for the electrical data 170. The mapping system 162 thus can generate corresponding output data 174 that can in turn be rendered as a corresponding graphical output in a display 192, such as including one or more electrocardiographic maps 192. For example, the map generator 188 can generate maps and other output visualizations, such as including but not limited to the maps and other output visualizations disclosed herein.

As an example, the map generator 188 can generate a map depicting a local connectivity association in response to the trajectory connectivity analyzer 182 applying distance (temporal and/or spatial) criteria to a connected trajectories to identify a set of connected trajectories that are less that a predetermined distance apart from each other. As another example, the map generator 188 can generate a map depicting a far connectivity association in response to the trajectory connectivity analyzer 182 applying different distance criteria to connected trajectories to identify a set of connected trajectories that are spaced apart from each other by a distance that exceeds far distance threshold. The map generator may generate a map depicting intermediate connectivity associations in response to the trajectory connectivity analyzer 182 identifying a set of connected trajectories that are spaced apart from each other by a distance that between the near and far thresholds. The visualization engine may provide separate maps for different types of connectivity associations. In other examples, the visualization engine may graphically differentiate different types of association and display multiple types of associations concurrently in a given map. The trajectory connectivity analyzer 182 and/or the visualization engine 188 further may prioritize one of the predetermined connectivity associations for trajectories over others, such as based on a type or arrhythmia, such as in response to a user input (via GUI 190) or other information specifying an underlying type of arrhythmia, such as disclosed herein.

Additionally, in some examples, the output data 174 can be utilized by the therapy system 158. For instance, the control system 160 may implement fully automated control, semi-automated control (partially automated and responsive to a user input) or manual control based on the output data 174. In some examples, the control 160 of the therapy system 158 can utilize the output data 174 to control one or more therapy parameters. As an example, the control 160 can control delivery of ablation therapy to a site of the heart (e.g., epicardial or endocardial wall) based on one or more arrhythmia drivers identified by the analyzer method 182. In other examples, an individual can view the map generated in the display to manually control the therapy system, such as using the identification location of connected trajectories (e.g., the region between connected trajectories) on the graphical map as a treatment site. Other types of therapy and devices can also be controlled based on the output data 174 and corresponding graphical map 194.

FIGS. 4-8 depict examples of graphical maps that can be generated (e.g., by output generator 30 or mapping system 162) to visualize on a display (e.g., 30 or 194) to demonstrate connected trajectories and associated connectivity characteristics superimposed on a geometric surface (cardiac envelope) for a heart model. In these examples, the heart model includes a mesh surface of nodes interconnected by edges, as described herein. In other examples, different models could be utilized. Additionally, each of the maps may be combined together or selectively switched between in response to a user input for one or more time intervals. The intervals can be consecutive intervals or be selected intervals (automatically selected or selected in response to a user input).

Figure 4:
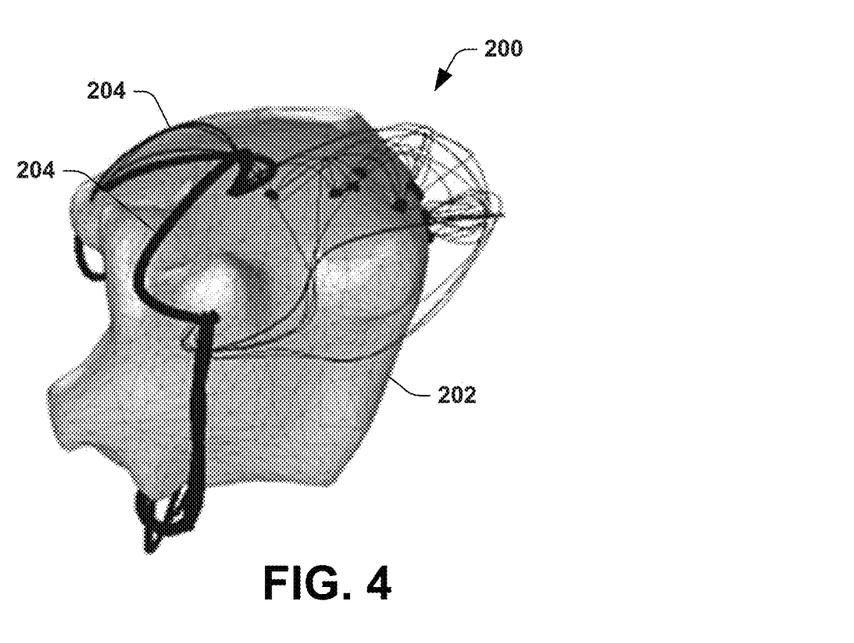
FIG. 4 depicts an example of a graphical map demonstrating connectivity between trajectories.

FIG. 4 depicts an example of a graphical map 200 of a heart 202 demonstrating connectivity between trajectories determined over a plurality of different time intervals. In this example, connectivity between each trajectory pair is demonstrated by an arc 204 that extends between each trajectory pair. For instance, bolder (thicker) lines thus may be used to visually indicate longer times for pairing among connected trajectories, while relatively thinner lines indicate shorter pairing times. In other examples, different graphical features or color scales may be used to indicate relative differences in trajectory pairing times (e.g., determined by connectivity characterization function 22 or analyzer 182).

Figure 5:
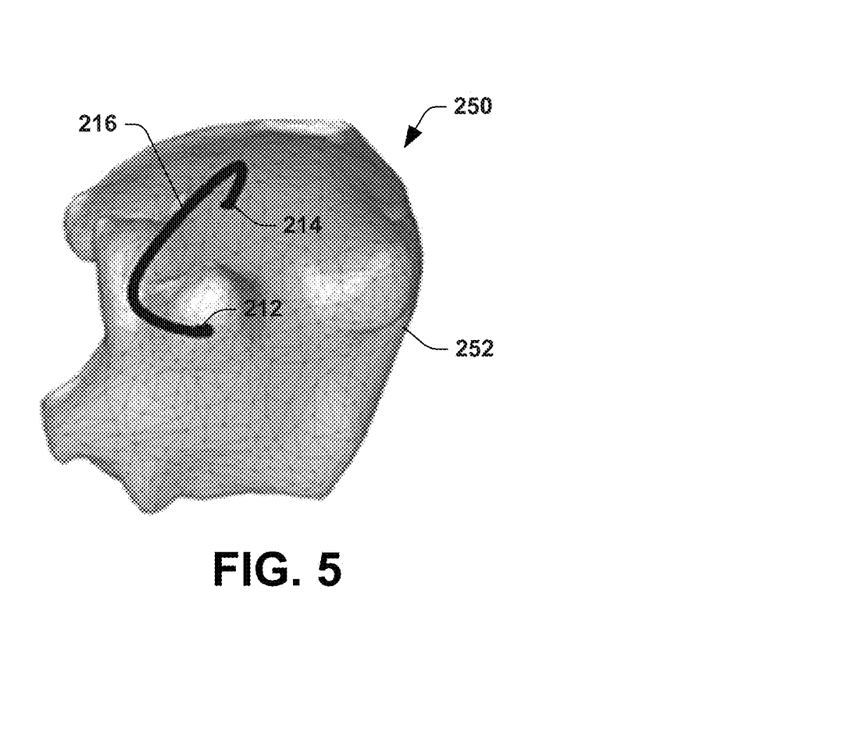
FIG. 5 depicts an example of a graphical map demonstrating connected trajectories over a plurality of different time intervals.

FIG. 5 depicts an example of a graphical map 210 demonstrating a pair of connected trajectories 212 and 214. The trajectories 212 and 214 in this example demonstrate local connected trajectory pairs (e.g., determined by connectivity characterization function 22 or analyzer 182). For example, the local connected trajectory pairing may be determined based on a computed distance between the connected trajectories that is less than a local distance threshold, as disclosed herein.

Figure 6:
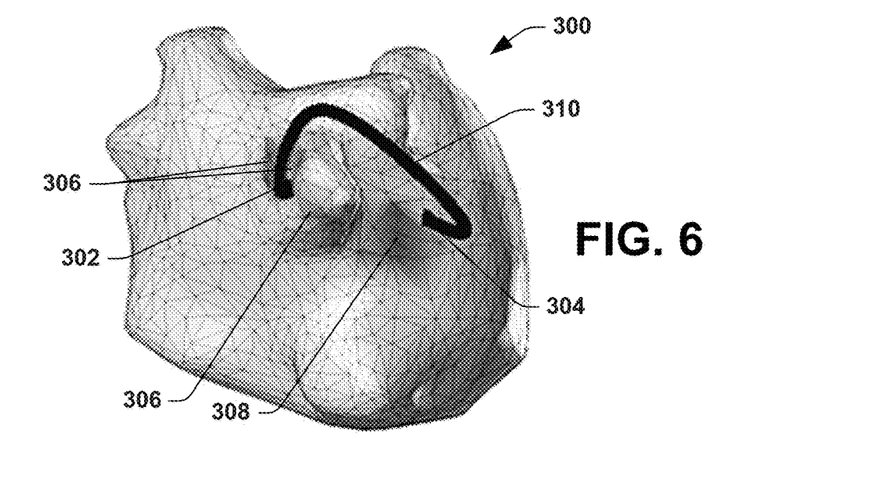
FIG. 6 depicts an example of a graphical map demonstrating connected trajectories and rotation cores.

FIG. 6 depicts an example of a graphical map 300 demonstrating connected trajectories 302 and 304 in combination with a graphical representation of rotation cores 306 and 308 mapped across the cardiac envelope. The connectivity between trajectories 302 and 304 is demonstrated via graphical arc 310 rendered (e.g., as a spline curve) between the trajectories.

Figures 7, 8:
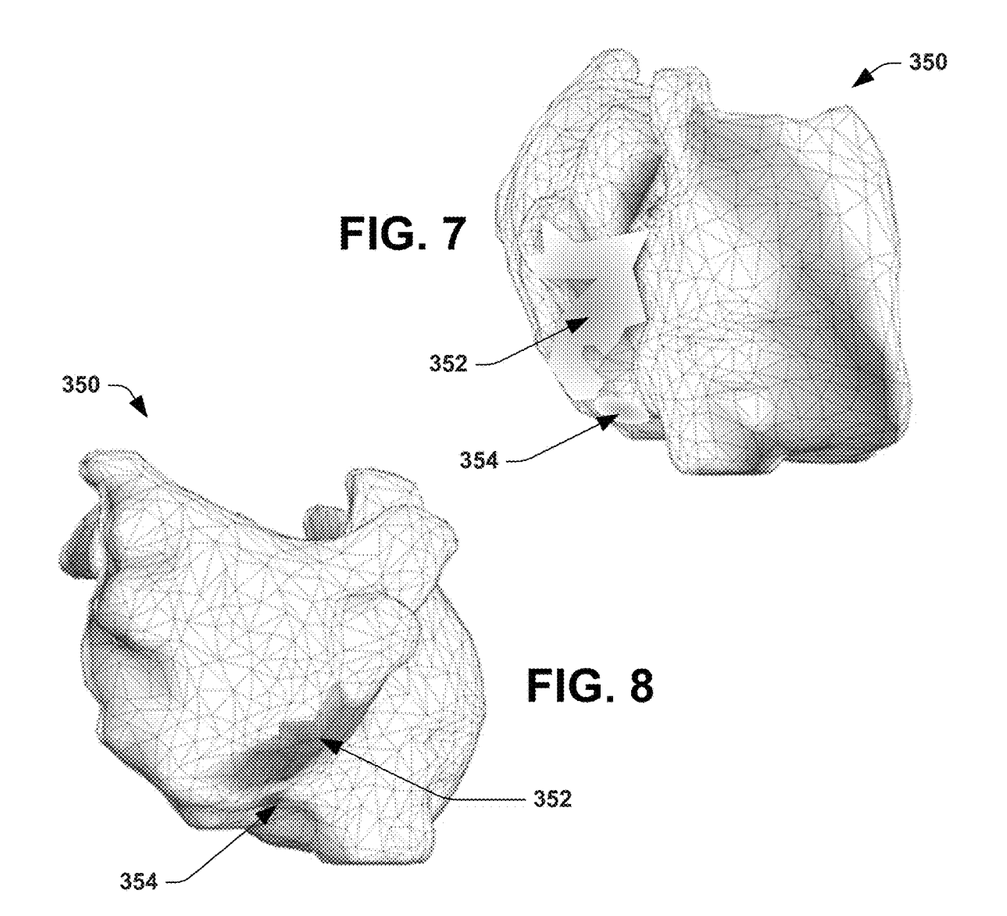
FIG. 7 depicts an example of a graphical map demonstrating a local connectivity association between connected trajectories over a plurality of different time intervals.
FIG. 8 depicts an example of a graphical map demonstrating the local connectivity association between trajectories from another view for the map of FIG. 7.

FIGS. 7 and 8 depict different views of a graphical map 350 showing a local connectivity association for a trajectory pair that has been aggregated over a plurality of time intervals. FIG. 7 depicts an example of a graphical map demonstrating local connectivity association between trajectories over a plurality of different time intervals. FIG. 8 depicts an example of a graphical map demonstrating another view of the same local connectivity association between trajectories from another view for the map of FIG. 7. For example, the local connectivity association demonstrated may be one type (local) of a multiple connectivity associations that is being prioritized and rendered on the display over other connectivity pairings that might exist, such as disclosed herein.

Figure 9:
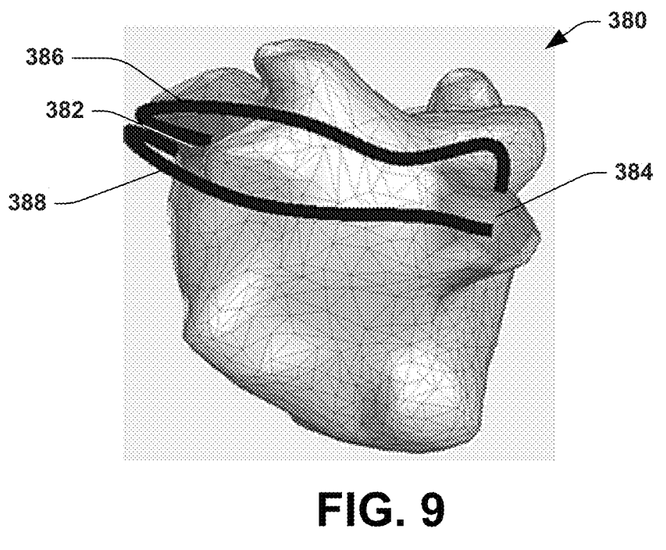
FIG. 9 depicts an example of a graphical map demonstrating a far connectivity association between connected trajectories over a plurality of different time intervals.
Figure 10:
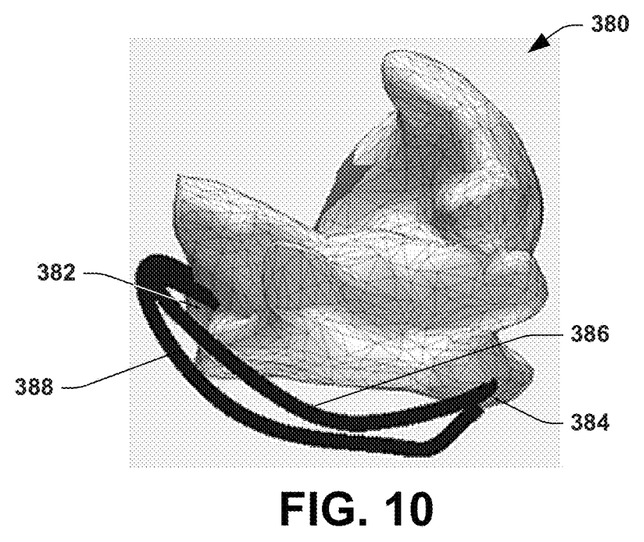
FIG. 10 depicts an example of a graphical map demonstrating the far connectivity association between trajectories from another view for the map of FIG. 9.

FIGS. 9 and 10 depict different views of a graphical map 380 showing a far connectivity association for a trajectory pair that has been aggregated over a plurality of time intervals (similar to the local association of FIGS. 7 and 8). In FIG. 9, a posterior-anterior view of the heart demonstrates a graphical map showing far connectivity associations for connected trajectories over a plurality of different time intervals. FIG. 10 depicts an example of the graphical map demonstrating another view (top view) of the same local connectivity associations between trajectories. In the example of FIGS. 9 and 10, the far associations are identified according to a distance threshold of 5 cm and a minimum connection time of 300 ms. As mentioned, different thresholds (default or user programmable) could be used to establish temporal and spatial distance criteria for identifying connected trajectories that are far apart.

Figure 11:
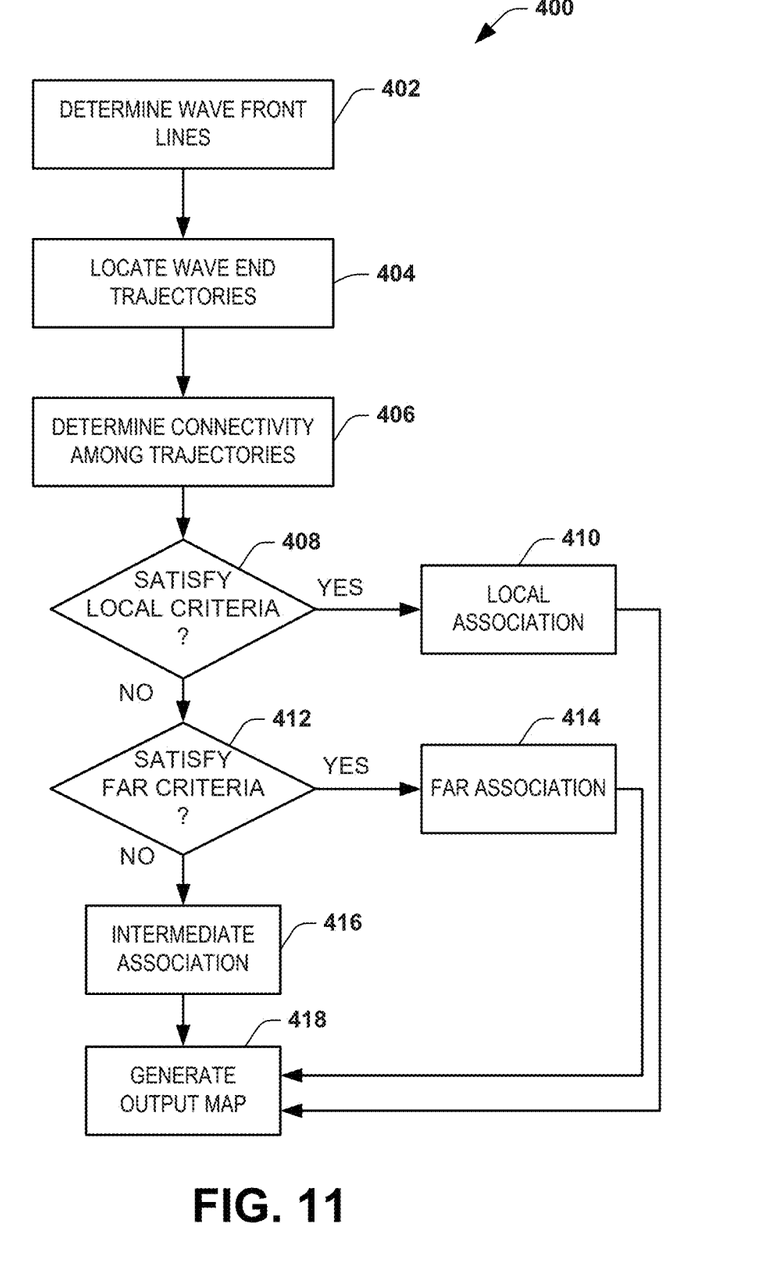
FIG. 11 is a flow diagram depicting an example of a method for analyzing and detecting connectivity among arrhythmia drivers.

In view of the foregoing structural and functional features described above, a method that can be implemented will be better appreciated with reference to FIG. 11. While, for purposes of simplicity of explanation, the method of FIG. 11 is shown and described as executing serially, it is to be understood and appreciated that such method is not limited by the illustrated order, as some aspects could, in other embodiments, occur in different orders and/or concurrently with other aspects from that shown and described herein. Moreover, not all illustrated features may be required to implement a method. The method or portions thereof can be implemented as instructions stored in one or more non-transitory storage media as well as be executed by a processing resource (e.g., one or more processor cores) of a computer system, for example.

FIG. 11 is a flow diagram depicting an example method 400 for detecting and analyzing connectivity associations for trajectories based on electrical data representing electrical activity distributed across a geometric surface (cardiac envelope) for one or more time intervals. The method begins at 402 to analyze (by wave front analyzer 16, 56) the electrical data and determine one or more wave front lines over a given time interval. For example, information describing the wave front lines can be stored in memory as wave front data, such as location data for nodes along each wave front line, timing information and related electrical phase values for the nodes (e.g., computed by phase calculator 66). At 404, respective trajectories for wave ends of each wave front line that has been determined across the cardiac surface are determined (e.g., by trajectory detector 18, 52 182) for time indices in the given time interval. For example, trajectories may be constructed for each wave end of the wave front lines according to the distance between wave ends in successive time frames of the given time interval.

At 406, connectivity among trajectories is determined (e.g., by connectivity detector 20, 182). For instance, a set of connected trajectories may is identified based on a duration that the trajectories remain connected to each other by a wave front line during the given time interval (or at least a portion thereof). For instance, temporal criteria may be applied to the duration trajectories are connected to ascertain whether wave end trajectories are connected.

At 408 through 416, a connectivity association is characterized (e.g., by connectivity detector 20, connectivity characterization function 22, trajectory connectivity analyzer 182) for each of the connected trajectories in the set of connected trajectories. As disclosed herein, there characterization can discriminate among a plurality of different types of predetermined connectivity associations, such as to specify a local connectivity association, a far connectivity association and an intermediate connectivity association. The discrimination can classify each of the connected trajectories by applying temporal and/or spatial criteria. By way of example, at 408, a determination is made whether local criteria is satisfied. For instance, this determination at 408 can include determining whether a computed distance is less than a local distance threshold and whether time of connectivity for the trajectories exceeds a temporal threshold. If the determination is positive (YES), indicating that the local temporal and spatial criteria is met, the method proceeds to 410 to characterize the connectivity association as a local connectivity association for the connected trajectories in response to determining that the distance is less than the first threshold. The association can be stored in memory (as metadata) to specify the type of connectivity association.

If the determination at 408 is negative (the local criteria is not met), the method proceeds to 412. At 412, a determination is made whether far criteria is satisfied. The far criteria may include spatial and time thresholds. As an example, the determination includes determining if the computed distance is greater than a far distance threshold and the time exceeds a temporal threshold. For instance, one or both far thresholds are different from the local thresholds applied at 408. In some examples, a common time threshold may be used but different distance thresholds. If the determination at 412 is positive (YES), indicating that the far criteria has been met, the method proceeds to 414 to characterize the connectivity association as a far connectivity association for the connected trajectories. Thus, in response to determining that the distance is exceeds the second threshold, the connectivity association for the set of connected trajectories can be specified as far.

If the determination at 412 is negative (neither the local or far criteria has been satisfied), the method proceeds to 416 to characterize the connectivity association for the set of connected trajectories as being intermediate (e.g., residing in between the first and second distance thresholds. Other criteria, which may involve more or less than three types classifications for connected trajectories, may be used. From 416 as well as from each of 410 and 414, the method proceeds to 418 to generate an output map to visualize connected trajectories and determined connectivity characteristics. As disclosed herein the maps may be static maps graphically representing connectivity information for trajectories on a cardiac envelope over one or more time intervals, which may be selected in response to a user input. Alternatively, the map generated at 418 may be dynamic (animated) showing how detected trajectories change across the cardiac envelope over time.

The locations of the trajectories and the region extending between the trajectories may be further graphically represented on the map as a target site (e.g., for applying ablation or other treatment). Localization methods may be employed to help guide a therapy device (e.g., device 156) to the identified target site for delivery of treatment. Changes in connected trajectories and trajectory connectivity characteristics in response to application of therapy to cardiac tissue (at specified target sites) may be used to provide visual feedback to the user about the success of such therapy and whether additional treatment is needed or the procedure may be terminated.

In view of the foregoing structural and functional description, those skilled in the art will appreciate that portions of the systems and method disclosed herein may be embodied as a method, data processing system, or computer program product such as a non-transitory computer readable medium. Accordingly, these portions of the approach disclosed herein may take the form of an entirely hardware embodiment, an entirely software embodiment (e.g., in a non-transitory machine readable medium), or an embodiment combining software and hardware. Furthermore, portions of the systems and method disclosed herein may be a computer program product on a computer-usable storage medium having computer readable program code on the medium. Any suitable computer-readable medium may be utilized including, but not limited to, static and dynamic storage devices, hard disks, optical storage devices, and magnetic storage devices.

Certain embodiments have also been described herein with reference to block illustrations of methods, systems, and computer program products. It will be understood that blocks of the illustrations, and combinations of blocks in the illustrations, can be implemented by computer-executable instructions. These computer-executable instructions may be provided to one or more processor of a general purpose computer, special purpose computer, or other programmable data processing apparatus (or a combination of devices and circuits) to produce a machine, such that the instructions, which execute via the processor, implement the functions specified in the block or blocks.

These computer-executable instructions may also be stored in computer-readable memory that can direct a computer or other programmable data processing apparatus to function in a particular manner, such that the instructions stored in the computer-readable memory result in an article of manufacture including instructions which implement the function specified in the flowchart block or blocks. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

What have been described above are examples. It is, of course, not possible to describe every conceivable combination of structures, components, or methods, but one of ordinary skill in the art will recognize that many further combinations and permutations are possible. Accordingly, the invention is intended to embrace all such alterations, modifications, and variations that fall within the scope of this application, including the appended claims. Where the disclosure or claims recite "a," "an," "a first," or "another" element, or the equivalent thereof, it should be interpreted to include one or more than one such element, neither requiring nor excluding two or more such elements. As used herein, the term "includes" means includes but not limited to, and the term "including" means including but not limited to. The term "based on" means based at least in part on.

What is claimed is:

1. One or more non-transitory computer-readable media having instructions executable by a processor, the instructions programmed to perform a method comprising:
analyzing electrical data to locate one or more wave front lines over a given time interval, the electrical data representing electrophysiological signals distributed across a spatial cardiac envelope within a patient's body for one or more time intervals;
determining a respective trajectory for each wave end of each wave front line that is located across the cardiac envelope over the given time interval;
identifying a set of connected trajectories based on a duration that the trajectories are connected to each other by a respective wave front line during the given time interval; and
characterizing a connectivity association for the trajectories in the set of connected trajectories.

2. The media of claim 1, wherein the method further comprises:
determining a distance between the trajectories in the set of connected trajectories; and
discriminating between a plurality of different types of predetermined connectivity associations for the set of connected trajectories based on the determined distance.

3. The media of claim 2, wherein discriminating between the plurality of different types of predetermined connectivity associations further comprises applying a spatial threshold to ascertain which one of the plurality of different types of predetermined connectivity associations characterizes the connectivity association.

4. The media of claim 3, wherein applying the spatial threshold further comprises applying multiple spatial thresholds to the determined distances to ascertain which one of the plurality of different types of predetermined connectivity associations characterizes the connectivity association.

5. The media of claim 4, wherein the plurality of different types of predetermined connectivity associations include a local connectivity association, a far connectivity association and an intermediate connectivity association, and
wherein the method further comprises:
specifying the local connectivity association for the set of connected trajectories in response to determining that the distance is less than a first threshold,
specifying the far connectivity association for the set of connected trajectories in response to determining that the distance exceeds a second threshold, and
specifying the intermediate connectivity association for the set of connected trajectories in response to determining that the distance is outside of the first and second thresholds.

6. The media of claim 1, wherein identifying connected trajectories further comprises:
determining the duration that the trajectories are connected to each other by the wave front line during the given time interval, and
wherein the trajectories are identified as being connected in response to determining that the duration that the trajectories are connected to each other during the given time interval exceeds a predetermined time period.

7. The media of claim 6, wherein the predetermined time period is programmable in response to a user input.

8. The media of claim 6, further comprising:
determining a spatial distance between the trajectories in the set of connected trajectories; and
specifying which type of connectivity association characterizes the connectivity association for the set of connected trajectories based on the determined distance relative to a spatial threshold and the duration that the trajectories are connected to each other during the given time interval relative to a time threshold, wherein the spatial threshold and/or the time threshold are programmable in response to a user input.

9. One or more non-transitory computer-readable media having instructions executable by a processor, the instructions programmed to perform a method comprising:
analyzing electrical data to locate one or more wave front lines over a given time interval, the electrical data representing electrophysiological signals distributed across a cardiac envelope for one or more time intervals;
determining a respective trajectory for each wave end of each wave front line that is located across the cardiac envelope over the given time interval;
identifying a set of connected trajectories based on a duration that the trajectories are connected to each other by a respective wave front line during the given time interval;
characterizing a connectivity association for the trajectories in the set of connected trajectories and
generating an output visualization to display the connected trajectories spatially on a graphical representation of a heart.

10. The media of claim 1, wherein the electrophysiological signals correspond to measured or reconstructed signals at a plurality of nodes distributed across the cardiac envelope for a plurality of time intervals,
wherein the method further comprises repeating the analyzing, determining, identifying and characterizing for each of the plurality of time intervals to characterize a respective connectivity association for each set of connected trajectories.

11. The media of claim 10, wherein the method further comprises generating an output visualization to display a representation of at least some of connected trajectories and/or connectivity associations spatially on a graphical representation of a heart.

12. The media of claim 11, wherein the method further comprises prioritizing one type of connectivity association relative to another type of connectivity association in the output visualization according to a cause of arrhythmia.

13. The media of claim 12, wherein the cause of arrhythmia is defined in response to a user input specifying the cause.

14. The media of claim 10, wherein the method further comprises discriminating between a plurality of different types of predetermined connectivity associations for each set of connected trajectories according to at least one of spatial and/or temporal criteria.

15. The media of claim 1, wherein the electrophysiological signals distributed across the cardiac envelope correspond to signals at nodes that are derived based on at least one of invasively acquired electrical signals for the patient or non-invasively acquired electrical signals for the patient.

16. A system comprising:
memory to store machine readable instructions and data, the data comprising store electrical data representing electrophysiological signals distributed across a cardiac envelope for one or more time intervals;
at least one processor to access the memory and execute the instructions, the instructions comprising:
a wave front analyzer that analyzes electrical data for a given time interval to identify a wave front line across the cardiac envelope;
a trajectory detector that detects a respective trajectory for wave ends of the wave front line over the given time interval;
a connectivity detector that identifies a set of connected trajectories according to a duration that the trajectories of wave ends are connected to each other by the wave front line over the given time interval;
a connectivity characterization function that applies spatial and/or temporal criteria to characterize a connectivity association for trajectories in the set of connected trajectories; and
an output generator that provides output data to drive a display with a graphical representation of the connectivity association for the trajectories in the set of connected trajectories.

17. The system of claim 16, wherein the connectivity characterization function determines a distance between the trajectories in the set of connected trajectories and discriminates between a plurality of different types of predetermined connectivity associations for the set of connected trajectories based on the determined distance.

18. The system of claim 17, wherein the connectivity characterization function is further programmed to apply a spatial threshold to the determined distance between each of the trajectories in the set of connected trajectories to ascertain which one of a plurality of different types of predetermined connectivity associations characterizes the connectivity association, the one of the plurality of different types of predetermined connectivity associations comprising one of a local connectivity association, a far connectivity association and an intermediate connectivity association.

19. The system of claim 18, wherein the connectivity characterization function is further programmed to:
specify the local connectivity association for the set of connected trajectories in response to determining that the distance is less than a first threshold,
specify the far connectivity association for the set of connected trajectories in response to determining that the distance exceeds a second threshold, and
specify the intermediate connectivity association for the set of connected trajectories in response to determining that the distance is outside of the first and second thresholds.

20. The system of claim 18, wherein the connectivity characterization function is further programmed to prioritize one plurality of different types of predetermined connectivity associations relative to another type of plurality of different types of predetermined connectivity associations according to a cause of arrhythmia, the output generator providing the output data to include the prioritized connectivity association in the graphical representation of the connectivity association.

21. The system of claim 16, further comprising:
an array of sensors to invasively and/or or non-invasively measure electrical activity from a patient's body; and
a measurement system to control measurements by the sensors and to provide the electrical data, the electrical data including measured and/or reconstructed electrophysiological signals at a plurality of nodes distributed across the cardiac envelope for a plurality of time intervals.

22. The media of claim 1, wherein the method further comprises providing output data to drive a display with a graphical representation of the connectivity association for the trajectories in the set of connected trajectories.

* * * * *